United States Patent [19]

McCue et al.

[11] 4,258,723

[45] Mar. 31, 1981

[54] BIOLOGICAL/PHARMACEUTICAL FLUID COLLECTION AND MIXING SYSTEM AND METHOD

[75] Inventors: John P. McCue, San Diego; Mogens L. Bramson, San Francisco, both of Calif.

[73] Assignee: SBR Lab, Inc., El Paso, Tex.

[21] Appl. No.: 928,411

[22] Filed: Aug. 1, 1978

[51] Int. Cl.³ ............................................. A61M 5/14
[52] U.S. Cl. ................................ 128/767; 128/214 B; 128/214 D
[58] Field of Search .................... 128/767, 760, 214 B, 128/214 D, 214.2; 141/35, 230, 323

[56] References Cited

U.S. PATENT DOCUMENTS

| 3,177,870 | 4/1965 | Salem, Jr. et al. | 128/214.2 |
|---|---|---|---|
| 3,467,095 | 9/1969 | Ross | 128/214.2 |
| 3,648,693 | 3/1972 | Koremura | 128/214 D |
| 3,664,814 | 5/1972 | Koremura | 128/214 D |

*Primary Examiner*—Willis Little
*Attorney, Agent, or Firm*—Jacques M. Dulin; James W. Potthast

[57] ABSTRACT

Blood collection apparatus, systems and methods for minimizing the lesion of collection caused by initial high volume ratios of anticoagulant fluid to blood at the beginning of known collection processes in which blood is passed into a collection bag containing the total amount of anticoagulant fluid for the entire amount of blood to be collected. A collection bag system has a bag containing the anticoagulant fluid which is passed to a blood collection bag at a rate determined by the flow rate of the blood into the collection bag to maintain the ratio of anticoagulant to blood at a level to minimize the lesion of collection throughout the collection process. The blood collection bag is suspended by a spring from a blood bag stand and the anticoagulant bag is supported by the stand in a fixed position. The bags are arranged on the stand and interconnected so that flow rate of anticoagulant is dependent upon the difference in levels of the blood and anticoagulant mixture in the collection bag and the anticoagulant in the anticoagulant bag. The collection bag is suspended from the stand by a spring to gradually lower the collection bag during the collection process and thereby maintain the difference between the levels at a desired value. In one embodiment, provision is made for mixing the blood and anticoagulant in a tube immediately prior to passing the mixture into the collection bag.

63 Claims, 4 Drawing Figures

BIOLOGICAL/PHARMACEUTICAL FLUID COLLECTION AND MIXING SYSTEM AND METHOD

BACKGROUND OF THE INVENTION

This invention relates generally to apparatus, systems and methods for collecting and mixing two biological/pharmaceutical liquids and, in particular, for collecting whole blood from a donor to minimize lesion of collection caused by unproportional mixing with anticoagulant fluids.

During conventional collection procedure, fresh, whole blood taken from a donor is passed to a collection bag already containing an amount of anticoagulant-storage or anticoagulant liquid needed to prevent the entire amount of blood to be collected from coagulating within the collection bag. These anticoagulants, such as ACD, CPD and CPD-Adenine, are strongly acidic, having a pH range of 4.95 to 5.63, and high in a complexing agent, citrate, that strips red cells of essential cations, $Ca^{+2}$ and $Mg^{+2}$. Customarily, a full unit or 450 ml of blood are mixed with 63-75 ml of anticoagulant.

The anticoagulant is present in full amount in the blood collection bag at the beginning of the process and whole blood is then mixed with this solution as it is collected. When the first approximately 100 ml of donor blood is drawn into the required volume of anticoagulant used for a full unit of stored blood, the red cells are initially subjected to an environment greatly altered from the one encountered in vivo and are irreparably damaged thereby. This damage to the red blood cells is referred to herein as the lesion of collection, although there are other factors causing lesion of collection.

This lesion of collection problem is discussed in "The Influence of Extra-Cellular Factors Involved in the Collection of Blood in ACD on Maintenance of Red Cell Viability During Refrigerated Storage" by John G. Gibson, et al., at p. 855 et seq. of the August 1956 issue of *The American Journal of Clinical Pathology*. Reference may be made to that paper for a thorough discussion of the problems. Briefly, Gibson found that this 100 ml of blood collected into the full volume of the anticoagulant solution underwent deleterious changes in their in vitro parameters, and that such changes correlated well with loss in post-transfusion survival of similarly treated red cells. Further, comparison of literature values indicated that post-transfusion survivals for full units of anticoagulant mixed whole blood were approximately the same after 21 days of storage as the volume percentage of whole blood found to be most injured during the initial stage of collection. These observations are reported to indicate that a significant contribution to loss in red cell post-transfusion viability and function results from the trauma induced during initial stages of collection of blood from the donor.

The anticoagulants have been carefully designed to minimize this lesion. However, for a number of technical reasons, no known anticoagulant fluid has been devised that completely eliminates this lesion of collection. Most work to date has been aimed at reducing the factors causing lesion during storage.

SUMMARY OF THE INVENTION

The principal object of the invention is provision of systems, apparatus and methods for reducing lesion of collection caused by mixing of large amounts of anticoagulant solution with small amounts of whole blood during the blood collection process.

The method following in accordance with the invention as applied to blood collection is to pass the fresh, whole blood into contact with anticoagulant fluid while controlling the rate of contact at a ratio of blood to anticoagulant which minimizes lesion of collection. Preferably, the rate is controlled by monitoring the weight or volume of blood, or mixture of blood and anticoagulant, and passing an amount of anticoagulant into contact in selected proportion to said weight or volume.

A container system employed in practicing the method of the invention has a first, anticoagulant container holding the required amount of anticoagulant needed for viable storage of the entire unit of blood to be collected; a mixing or collection container for receiving both the fresh, whole blood and the anticoagulant; a tube for passing fresh blood into the storage container; and a tube for passing a desired proportional amount of anticoagulant into the storage container from the anticoagulant container. In one embodiment, the anticoagulant is passed through a portion of the donor tube so that initial mixing occurs immediately prior to passage of the mixture into the collection container.

Apparatus constructed in accordance with the invention includes means for supporting the first container with a biological/pharmaceutical liquid, such as anticoagulant, at a first level, means for supporting a mixing container with the mixture of the anticoagulant and a second biological/pharmaceutical liquid, such as fresh, whole blood at a second level and means associated with at least one of the supporting means for controlling the difference between the levels by means for causing relative motion between the two containers in accordance with the weight of the liquid mixture in the mixing container. The two containers are interconnected by a tube attached at the bottoms thereof. The weight changes at a rate dependent upon the flow rate of the blood or the like and the flow rate of anticoagulant or the like is dependent upon the difference between the fluid levels.

The foregoing objects, features and advantages will be made more apparent and further objects, features and advantages will be described in the description of the preferred embodiments.

BRIEF DESCRIPTION OF THE DRAWING

The following description of the preferred embodiments will be given with reference to the following figures of the drawing, in which.

DESCRIPTION OF THE PREFERRED EMBODIMENTS

Figure 1:
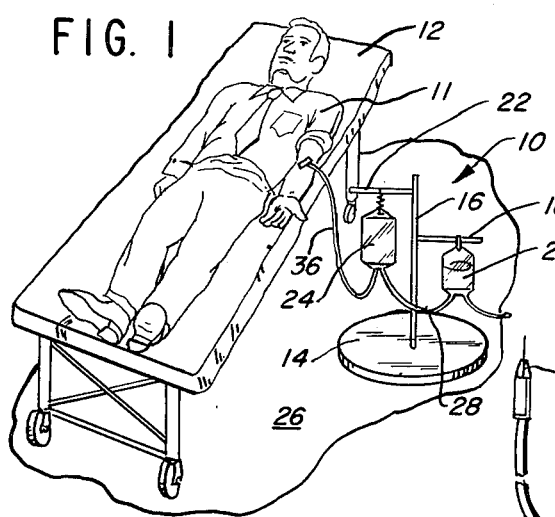
FIG. 1 illustrates an overall view of the apparatus as used in the blood collection process.

Referring to the drawing, particularly FIG. 1, the biological/pharmaceutical fluid collection and mixing system 10 is shown as being used to collect fresh blood from a donor 11. The blood donor 11 is shown lying down on his back on a hospital bed or platform 12 of conventional hospital bed height, e.g., approximately 30 inches. The system 10 is seen to include a base 14 in supportive underlying engagement with a vertical member or stand 16. A support 18 carried by vertical member 16 provides support to a first liquid container, such as bag 20. A second support 22 provides support for a second, mixing or collection container such as collection bag 24. The distance between the base 14, located on the floor 26 and support 22 is such that the collection bag 24 is located at a height no greater than that of the donor 11 atop bed 12 to facilitate blood flow to collection bag 24. The bottoms of bags 20 and 24 are interconnected by a tube 28. The collection bag 24 is, in turn, connected through a tube 30 and a suitable hollow needle 32, FIG. 2A, to the arm of donor 11.

Figure 2A:
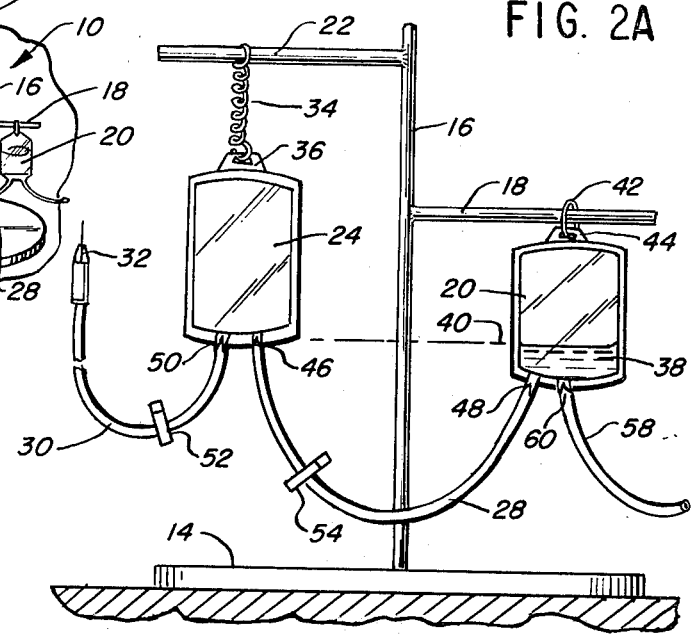
FIG. 2A is a side elevational view of one embodiment of the apparatus of the present invention at the beginning of the blood collection process.

Referring now to FIG. 2A, it is seen that storage bag 24 is suspended from support 22 by means of a resilient member such as tension spring 34. One end of spring 34 is releasibly attached to support 22 and the other end is releasibly attached to the tab 36 of storage bag 24. The first container or anticoagulant bag 20 contains a suitable amount of anticoagulant fluid, such as ACD, CPD, or CPD-Adenine 38 at a first level 40. Level 40 is approximately coincident with the bottom of collection bag 24 at the beginning of the collection process. During the collection process, spring 34 stretches as the weight of the liquid mixture in bag 24 increases. The anticoagulant bag 20, on the other hand, is releasibly, but rigidly, attached to support 18 by means of a suitable connector such as loop 42 extending through a loop or tab 44 at what is herein designated as the "top" of bag 20. Puncture seals 46 and 48 at opposite ends of anticoagulant inlet tube 28, and a puncture seal 50 at the juncture of donor tube 30 with bag 24 maintains the fluid integrity of the system until it is ready to use. Tube clamps 52 and 54 are employed to close tubes 30 and 28, respectively, before the puncture seals have been broken immediately prior to commencement of the collection process, which then occurs when clamps 52 and 54 are removed.

The amount of anticoagulant 38 held by anticoagulant bag 20 depends upon the type of anticoagulant being used and the amount of blood being collected. For collection of 450 ml of whole blood, anticoagulant bag 20 is provided with 63 ml of CPD, 67.5 ml of ACD, or 63 ml of CPD-Adenine. These amounts of anticoagulant are needed for optimum storage of 450 ml to 500 ml of blood. In practicing the invention, the anticoagulant is mixed with the blood during the collection process in a manner to maintain the ratio of anticoagulant to blood at a level for optimization of storage.

When blood from the donor is ready to be collected, the puncture seals are broken. Clamps 52 and 54 are released immediately after the phlebotomy needle 32 is placed in the arm of donor 11. When blood begins to flow from the donor, through needle 32 and donor tube 30, the increased weight of storage bag 24 causes it to lengthen spring 34. When the bottom of storage bag 24 falls below the fluid level 40 of the anticoagulant 38, anticoagulant fluid 38 begins to flow through tube 28 into collection bag 24. The flow of anticoagulant may occur slightly before blood enters the bag 24.

Figure 2B:
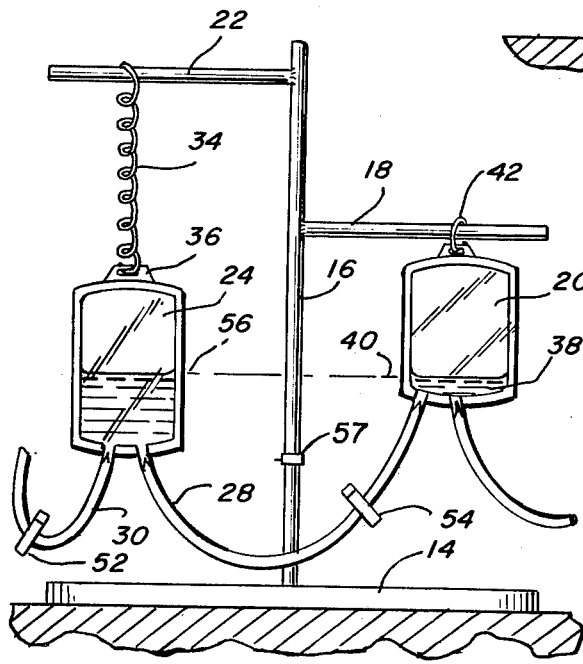
FIG. 2B is a side elevational view of the embodiment of FIG. 2A when approximately midway through the blood collection process.

Referring to FIG. 2B, it is seen that when approximately half of the desired 450 ml of blood has been collected, approximately half of the anticoagulant 38 has been transferred from anticoagulant bag 20 to collection bag 24. The flow rate of anticoagulant is a function of the difference between the level 40 of the anticoagulant and the level 56 of the blood and anticoagulant mixture in collection bag 24. The spring 34 functions to lower bag 24 as the weight of the liquid mixture therein increases to maintain the difference between levels 40 and 56 at a value which will maintain the flow rate of CPD anticoagulant at a rate on the order of 63/450's of the rate of flow of the blood into bag 24. The entire time required to collect approximately 450 ml of blood is approximately five to seven minutes, and in this time the anticoagulant bag 20 will empty its approximately 63 ml of anticoagulant into storage bag 24. Thus, the rate of anticoagulant flow is controlled by the rate of flow of donor blood. Should the collection process be interrupted, the weight of the collection bag 24 will not increase such that the flow of anticoagulant will also be interrupted. Likewise, should the rate of flow of blood vary, the rate of flow of anticoagulant will vary accordingly. The ratio will vary with the type of anticoagulant.

In experiments with a particular system constructed in accordance with the invention as described herein, the levels 40 and 56 were maintained approximately coincident or with level 40 slightly above level 56 to achieve the desired amount of flow. Specifically, a stand was constructed employing a "blood-pack" bag system available from Fenwal Laboratories. In this system, the collection bag is approximately 7¾ inches in length and sized to receive approximately 600 ml of liquid. A "transfer pack" bag available from Fenwal Corporation was used for anticoagulant bag 20. This bag is sized to receive approximately 300 ml of liquid and is approximately 5⅛ inches in length. The spring 34 has approximately 32 coils of stainless steel wire of approximately 0.032 inches in diameter and a coil length of approximately 1.025 inches. The length of the spring at maximum extension was 12.5 inches and the spring rate was 0.1 pounds per inch. The distance between support 18 and support 22 was 6.0 inches. Standard tubing for use with these bags was used for tubes 28 and 30. As seen in FIGS. 2A and 2B, the storage bag 20 can be provided with an additional tube 58 attached to the bottom of bag 20 through a puncture seal 60 for filling the bag 20 with anticoagulant or for withdrawing fluid from the bag which may be subsequently collected therein. In particular, after the blood is collected, the empty anticoagulant bag 20 may be used to collect plasma for preparation of packed red cells and plasma components.

Figure 3:
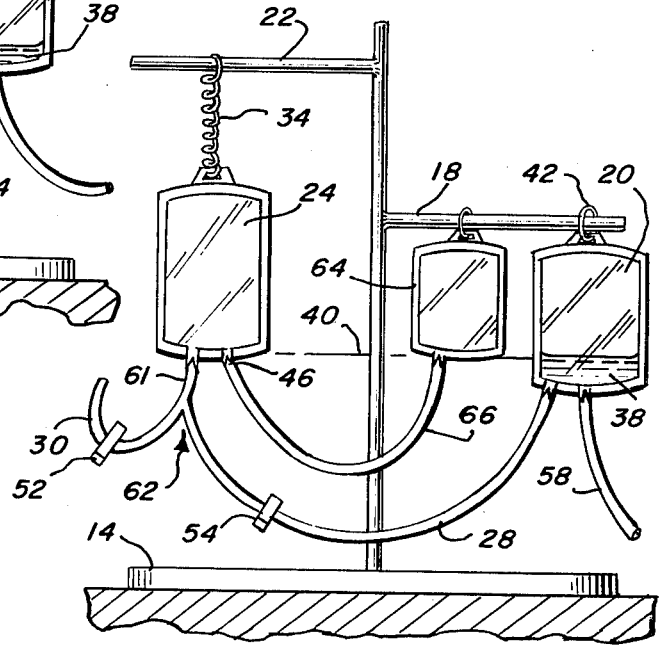
FIG. 3 is a side elevation of another embodiment of the apparatus.

Referring to FIG. 3, another embodiment is shown in which tube 28 is connected to collection bag 24 through a portion 61 of tube 30 adjacent the bottom of bag 24 by means of a "T" joint 62. This allows anticoagulant fluid 38 to mix with the donor blood within tube portion 61 instead of in bag 24. An additional bag 64 in lieu of empty anticoagulant bag 20 may be provided for separating the plasma from the whole blood through centrifuging. Bag 64 is connected to the port with puncture seal 46 through a suitable plastic tube 66. Tube 66 is not inserted through puncture seal until the blood donor process has been completed and the plasma has been centrifuged.

As can be seen from the figures and the above description, the blood collection method of this invention includes withdrawing blood from the donor, passing this blood into contact with an anticoagulant fluid, and controlling the rate of contact of the blood with the anticoagulant, preferably by the level control, at a ratio of blood to anticoagulant which minimizes the lesion of collection. This rate is preferably controlled within a tolerance of ±20% during withdrawal, and is 7.14±1.42 for CPD anticoagulant, 6.67±1.33 for ACD, and 7.14±1.42 for CPD-Adenine. This ratio is substantially the same as the amount of blood supposed to be collected for the approved amount of given anticoagulant for blood storage purposes (4° C.). Since the blood and anticoagulant have readily ascertainable densities, are relatively uniform during withdrawal, and do not vary excessively from donor to donor, the ratio may be expressed and controlled in relation to volume rather than weight. We also prefer to wet the main bag 24 with a thin film of anticoagulant. This may be done by placing or sealing a few ml of anticoagulant into the main bag 24 during bag manufacture, or introducing a few ml of anticoagulant therein just prior to venipuncture of the donor. It should be understood that any anticoagulant solution may be used, whether currently approved or those which may become approved and which may contain an effective amount of a blood storage improving additive, such as dihydroxyacetone, inosine, pyruvate, glucose, a pH control agent or means, ATP or the like.

We claim:

1. Apparatus for entering a first biological/pharmaceutical liquid of a first container into a mixing container through a tube at a rate controlled by the rate of entry into the mixing container of a second biological/pharmaceutical liquid, comprising:

means for supporting the first container with the first liquid therein at a first liquid level;

means for supporting the mixing container with the mixture of the first and second liquids therein at a second liquid level, the flow rate of said first liquid being dependent upon the difference between said first and second levels; and means associated with at least one of the supporting means and the container supported thereby for controlling the difference between said first and second levels, said controlling means including means for automatically causing relative motion between the container of said one supporting means and the container of the other supporting means in response to and in accordance with the weight of the liquid in the mixing container, said weight changing at a rate dependent upon the flow rate of the second liquid.

2. The apparatus of claim 1 in which said first biological/pharmaceutical liquid is a blood anticoagulant fluid and said second biological/pharmaceutical liquid is whole blood.

3. The apparatus of claim 1 in which said second biological/pharmaceutical liquid is whole blood.

4. The apparatus of claim 3 in which the whole blood is being drawn from a blood donor at a relatively unregulated rate, and the flow rate of the first liquid varies with the variation in said relatively unregulated rate.

5. The apparatus of claim 3 in which the apparatus has a base above which said mixing container is supported and the distance between the mixing container when empty and the base is no greater than the height of a standard hospital bed.

6. The apparatus of claim 1 in which said controlling means is associated with the mixing container supporting means.

7. The apparatus of claim 6 in which said relative motion causing means permits the mixing container to automatically move downwardly as the weight of the liquid therein increases.

8. The apparatus of claim 7 in which the relative motion causing means permits the mixing container to move in proportion to the changing weight of the liquid in the mixing container.

9. The apparatus of claim 7 in which said mixing container supporting means includes a rigid member and said moving means includes a resilient member connected to said rigid member and in movable supportive engagement with the mixing container.

10. The apparatus of claim 9 in which said mixing container is movably suspended from said rigid member by said resilient member.

11. The apparatus of claim 10 in which said resilient member comprises a spring.

12. The apparatus of claim 7 in which said first container supporting means holds the first container in a relatively fixed position.

13. The apparatus of claim 12 including a base and a vertical member in supportive overlying engagement with the base and in which said first container supporting means includes a first rigid support member carried by the vertical member at a location spaced from the base and adapted for supportive attachment to the first container, and said mixing container supporting means includes a second rigid support member carried by the vertical member at a location spaced from both the base and the first rigid support member.

14. The apparatus of claim 13 including a marker selectively positionable along the vertical member.

15. The apparatus of claim 13 in which both said first and second rigid support members are adapted for suspension therefrom of said containers.

16. The apparatus of claim 1 in which said controlling means substantially maintains a fixed selected difference between said first and second liquid levels for facilitating a substantially constant relative flow rate of said first and second liquids.

17. The apparatus of claim 16 in which said difference is approximately nil.

18. The apparatus of claim 16 in which said difference is that amount necessary to maintain a ratio of flow rate of the first liquid to the flow rate of the second liquid of approximately 63:450 when the first liquid is CPD anticoagulant fluid and the second liquid is whole blood.

19. A controlled biological/pharmaceutical liquid mixing system, comprising:

a first container with a bottom holding a selected amount of a first biological/pharmaceutical liquid;

a mixing container with a bottom;

a tube connecting the bottoms of the first container and the mixing chamber;

a second tube connected to the bottom of the mixing container for passage of a second biological/pharmaceutical liquid into the mixing container;

means for supporting the first container with the first biological/pharmaceutical liquid at a first level;

means for supporting the mixing container with the liquid mixture therein at a second level; and means associated with at least one of the supporting means and the container supported thereby for causing said the container supported thereby to automatically move in accordance with the changing weight of the liquid held in the mixing container to control the rate of flow of said first liquid.

20. The system of claim 19 in which the first biological/pharmaceutical liquid is blood anticoagulant storage fluid.

21. The system of claim 19 in which said mixing container is sized to receive a selected amount of whole blood in addition to all of said anticoagulant fluid and said selected amount of anticoagulant is approximately 63/450 of the selected amount of whole blood.

22. The system of claim 21 in which said selected amount of anticoagulant fluid is approximately 63 ml.

23. The system of claim 19 in which the rate of flow is a function of the difference between said first and second levels, and said causing means controls the rate of flow of said second liquid by controlling the difference between said levels.

24. The system of claim 23 in which said causing means is associated with the mixing container supporting means and permits the mixing container to move downward in relation to the first container as the weight of the liquid in the mixing container increases.

25. The system of claim 24 in which said causing means comprises a resilient member.

26. The system of claim 25 in which the mixing container is supported by said resilient member.

27. The system of claim 26 in which said resilient member is a spring.

28. The system of claim 19 in which each of said first container and said mixing container are bags.

29. The system of claim 19 in which said second tube has an open end and a hollow needle attached thereto adapted for venipuncture.

30. The system of claim 19 including a base, a vertical member in supported, overlying engagement with the base, and in which said first container supporting means includes a first support carried by the vertical member and spaced from the base and means for releasibly suspending the first container from the first support, said mixing container supporting means includes a second support carried by the vertical member and spaced from both the base and the first support, said causing means includes a resilient member with two ends, means for attaching one end to the second support and means for attaching the other end to said mixing container, said mixing container being suspended from said second support by said resilient member.

31. The system of claim 30 in which said second support is intermediate the first support and the base.

32. The system of claim 30 in which each of said first container and said mixing container are water impermeable bags and all said connecting tubes are plastic.

33. The system of claim 30 in which said first biological/pharmaceutical liquid is a blood anticoagulant liquid.

34. The system of claim 30 including means for releasibly closing each of said tubes.

35. The system of claim 30 including an ancillary container connected to the mixing container through another tube and means for releasibly attaching said ancillary container to one of said first and second supports.

36. The system of claim 30 in which said tube connecting the bottoms of the first container and the mixing container connects the containers through a portion of said second tube said connection being made at a point spaced from the bottom of said mixing container.

37. The system of claim 36 in which said portion is adjacent the bottom of the mixing container.

38. The system of claim 37 in which said first and second liquids mix in said portion before passing into the mixing container.

39. The system of claim 30 in which the tube interconnecting the first container and the mixing container has a puncture seal at each of opposite ends thereof.

40. The system of claim 19 in which said tube connecting the bottoms of the first container and the mixing container connects the containers through a portion of said second tube, said connection being made at a point spaced from the bottom of said mixing container.

41. The system of claim 40 in which said portion is adjacent the bottom of the mixing container.

42. The system of claim 41 in which said first and second liquids mix in said portion before passing into the mixing container.

43. Apparatus for collection and storage of blood comprising:
 a first container bag holding a selected amount of anticoagulant liquid;
 a second container bag having only a slight amount of anticoagulant liquid obtained by wetting the inside surface thereof;
 a flexible tube interconnecting the bottoms of the bags;
 another flexible tube connected to the second container at one end and connected to a hollow needle at the opposite end.

44. The apparatus of claim 43 in which the first container holds approximately 63 ml of anticoagulant liquid.

45. The apparatus of claim 43 in which said other flexible tube is connected to the bottom of the second container and said first mentioned flexible tube interconnects the first and second containers through a portion of the other tube.

46. The apparatus of claim 45 in which said portion is adjacent the bottom of the second bag.

47. The apparatus of claim 43 in which each of said containers comprise flexible plastic bags.

48. The apparatus of claim 43 including a third bag and a tube interconnecting the third container and the first container.

49. A method of blood collection comprising the steps of:
 (a) withdrawing fresh blood from a donor;
 (b) passing said freshly drawn blood into contact with an anticoagulant fluid; and
 (c) automatically controlling the rate of contact of said blood with said anticoagulant at a ratio of blood to anticoagulant which minimizes the lesion of collection.

50. Blood collection method as in claim 49 wherein said rate-controlling step includes: maintaining said ratio within a tolerance of ±20% during the withdrawal of said blood.

51. Blood collection method as in claim 50 wherein said rate of contact ratio of blood to anticoagulant is substantially the same as the ratio of blood to anticoagulant for storage.

52. Blood collection method as in claim 51 wherein said anticoagulant is selected from the group consisting essentially of ACD, CPD, CPD-Adenine, and an anticoagulant containing an effective amount of a blood storage improving additive.

53. Blood collection method as in claim 52 wherein said ratio is about 500 ml blood to 75 ml anticoagulant.

54. Blood collection method as in claim 54 wherein said anticoagulant is ACD.

55. Blood collection method as in claim 52 wherein said ratio is about 450 ml blood to 63 ml anticoagulant.

56. Blood collection method as in claim 55 wherein said anticoagulant is CPD.

57. Blood collection method as in claim 52 wherein said ratio is about 450 ml blood to 63 ml anticoagulant.

58. Blood collection method as in claim 57 wherein said anticoagulant is CPD-Adenine.

59. Blood collection method as in claim 50 wherein said rate-controlling step includes:
  (a) weighing the amount of blood withdrawn, and
  (b) passing an amount by weight of anticoagulant into contact with said blood in inverse proportion to a unit weight of blood times said blood/anticoagulant ratio.

60. Blood collection method as in claim 50 wherein said rate-controlling step includes:
  (a) monitoring the amount of the blood withdrawn, and
  (b) passing an amount by volume of said anticoagulant into contact with said blood in inverse proportion to a unit weight of blood times said blood/anticoagulant ratio and the ratio of densities of blood and anticoagulant.

61. Blood collection method as in claim 50 wherein said step of passing said blood into contact with anticoagulant includes:
  (a) introducing said blood into a sterile blood collection unit plastic main bag through a first tube, and
  (b) simultaneously introducing said ratioed amount of anticoagulant into said plastic main bag through a second tube.

62. Blood collection method as in claim 61 which includes the step of:
  (a) wetting the surface of said plastic main bag with a thin film of anticoagulant prior to said introduction of said blood thereinto.

63. The apparatus of claim 43 in which each of said bags has a top opposite the bottom and means at said top for releasable connection to a suitable connector for suspending the bag therefrom.

* * * * *